United States Patent [19]
Stormo

[11] Patent Number: 5,744,105
[45] Date of Patent: *Apr. 28, 1998

[54] SLURRY REACTOR

[75] Inventor: Keith Stormo, Moscow, Id.

[73] Assignee: Innovative BioSystems, Inc., Moscow, Id.

[ * ] Notice: The term of this patent shall not extend beyond the expiration date of Pat. No. 5,616,304.

[21] Appl. No.: 708,120

[22] Filed: Sep. 3, 1996

Related U.S. Application Data

[63] Continuation of Ser. No. 426,566, Apr. 21, 1995, Pat. No. 5,616,304.

[51] Int. Cl.$^6$ ............... B01F 13/02; B01F 7/20; C12M 1/06
[52] U.S. Cl. ............ 422/227; 435/290.2; 435/289.1; 435/300.1; 366/170.3; 266/235
[58] Field of Search ................. 422/184, 225, 422/227, 231; 435/262.5, 290.2, 289.1, 300.1; 366/167.2, 168.1, 168.2, 169.1, 170.3, 170.4, 172.1, 172.2, 170.2; 266/233, 235; 239/142, 143, 251, 263, 566, 556, 557

[56] References Cited

U.S. PATENT DOCUMENTS

| | | | |
|---|---|---|---|
| 1,478,222 | 12/1923 | Hansen | 366/170.3 |
| 1,527,404 | 2/1925 | Haller et al. | 366/170.3 |
| 3,152,982 | 10/1964 | Pagnotti | 210/7 |
| 4,728,082 | 3/1988 | Emmett, Jr. et al. | 266/168 |
| 4,732,608 | 3/1988 | Emmett, Jr. et al. | 75/101 R |
| 4,974,816 | 12/1990 | Emmett, Jr. et al. | 266/168 |
| 5,007,620 | 4/1991 | Emmett, Jr. et al. | 266/168 |
| 5,034,131 | 7/1991 | Stenroos et al. | 210/612 |
| 5,055,204 | 10/1991 | Bogart | 210/758 |
| 5,057,284 | 10/1991 | Emmett, Jr. et al. | 422/225 |
| 5,061,080 | 10/1991 | MacKay et al. | 366/168.2 |
| 5,102,803 | 4/1992 | Weaver | 422/184 |
| 5,227,136 | 7/1993 | Hanify et al. | 422/277 |
| 5,342,429 | 8/1994 | Yu et al. | 266/235 |
| 5,616,304 | 4/1997 | Stormo | 422/227 |

OTHER PUBLICATIONS

Stormo, K.E. and Deobald, L.A., "Novel Slurry Bioreactor with Efficient Operation and Intermittent Mixing Capabilities", *Biological Unit Processes for Hazardous Waste Treatment*, edited by Hinchee, Oct., 1995, pp. 129–135.

Copy of Poster Board Presentation at the *Third International In–Situ and On–Site Bioremediation Symposium*, San Diego, California, Apr. 25–Apr. 26 1995

*Primary Examiner*—Robert J. Warden
*Assistant Examiner*—Elizabeth Dawson
*Attorney, Agent, or Firm*—Ken J. Pedersen; Barbara S. Pedersen

[57] ABSTRACT

Embodiments of a slurry reactor and slurry mixer/contactor are shown and described. Each embodiment of the reactor includes a vessel for containing a liquid slurry or suspension of particles and microorganisms. In the inside of the vessel, generally along its centerline, is a vertical conduit extending from near the top to near the bottom. At the bottom of the vertical conduit is at least one generally horizontal, hollow, stirrer blade in fluid connection with the vertical conduit. The stirrer blade is a mixer/contactor which has openings near its leading edge so fluid may pass therethrough. The stirrer blade may rotate around the vertical conduit if the conduit is fixed, or the conduit, with the stirrer blade fixed to it, may rotate around in the vessel. In any event, the rotation of the stirrer blade is caused by the hydraulic forces of fluid flowing out from the stirrer blade. The flowing fluid creates a fluidization zone in the slurry sediment bed at the leading edge of the stirrer. The fluidization zone is less dense than the rest of the sediment bed, and the stirrer blade tends to rotate into the fluidization zone. This way, controlled rotation of the stirrer blade may be created near the bottom of the vessel, enhancing mixing of the slurry or suspension in the vessel, without unnecessarily damaging the microorganisms.

28 Claims, 7 Drawing Sheets

SLURRY REACTOR

DESCRIPTION

This application is a continuation of my prior application, entitled "Slurry Reactor", Ser. No. 08/426,566, filed Apr. 21, 1995, now U.S. Pat. No. 5,616,304, which is hereby incorporated herein.

The U.S. Government has a paid-up license in this invention and the right in limited circumstances to require the patent owner to license others on reasonable terms as provided for by the terms of contract No. N47408-93-C-7359, awarded by the U.S. Navy.

BACKGROUND OF THE INVENTION

1. Field of the Invention

This invention relates to reactors and to reactor systems in general, and more specifically, to a mixer/contactor for a slurry reactor system. The mixer/contactor is advantageous for slurry processes wherein contact time may be relatively long, and/or wherein minimum energy input for suspending and mixing the slurry is desired, for example, in the biological remediation of contaminated sludges or soils.

2. Related Art

Slurry reactors are commonly used for processing ores, soils, and wood chips. Also, they are commonly used to effect the biological, enzymatic or chemical conversion of soluble and insoluble reactants. A slurry is a mixture of a liquid and solid particles, wherein at least a portion of the solid particles are suspended in the liquid. Especially, there is a large need to remediate sludges or soils contaminated with chemicals. These chemicals may be organic or inorganic, and hazardous or toxic. Many millions of cubic feet of soils contaminated with these chemicals exist throughout the world.

Biodegradation of many of these contaminating chemicals has been conducted. "Biodegradation" means breaking down these chemicals to less hazardous or less toxic reaction products via biological pathways using microorganisms. The microorganisms may operate aerobically or anaerobically. Also, the microorganisms may operate via oxidative pathways or reductive pathways. Microorganisms include bacteria, protozoa, fungi and algae. Biodegradation of soils contaminated with chemicals is one way to remediate the soil.

Often, the remediating microorganisms operate on the contaminating chemicals in a slurry environment in a reactor vessel, wherein the soil is mixed with water to at least partially suspend the soil particles for intimate contact with the microorganisms. To further increase suspension, mixing and contacting, a gas, such as air in aerobic applications, for example, may be added to the reactor vessel. When the reactor vessel contains microorganisms and a slurry, it is referred to as a bioslurry reactor.

Presently, at least four bioslurry reactor systems are being commercialized for soil remediation. The first system, developed by MOTEC, Inc. of Mt. Juliet, Tenn., involves technology adapted for treatment of pesticides, PCB's, dioxin and halogenated and nonhalogenated organic compounds. While demonstrated to be effective for treating sludge, liquids and soils having high organic concentrations, the MOTEC process has been reported to be less suitable for use with inorganic-laden wastes.

The MOTEC technology, which is a sequential process, is also referred to as liquid solid contact digestion (LSCD). The system involves two to three tank digestors which are aerated using air spargers and are agitated using turbine mixers. Alternatively, this technology may be adapted, by use of high shear propeller mixers, to enhance aerobic biological degradation in lagoons.

The second technology, developed by Detox Industries, Inc. of Sugarland, Tex., is intended for use in treating chlordane, myrex, oil, phenolics, polycyclic aromatic hydrocarbons, creosote, pentachlorophenol (PCP) and polychlorinated biphenyls (PCB's). The Detox system includes an open-topped reaction tank or on-site created lagoon that utilizes a synthetic liner. The tank is adapted to retain a slurry and is fitted with air distributors.

Another bioslurry reactor, consisting of several agitated and aerated vessels, has been used in a pesticide spill application by ECOVA of Redmund, Wash.

The MOTEC, Detox, and ECOVA systems described above are operated in batch mode. After the placement of contaminated soil and water into the reactor vessel, the vessel is aerated until a desired residual contaminant level is reached, and then the supernatant water is usually recycled and the slurry is discharged. Due to the ongoing aeration in these systems, many volatile organic substances are not biodegraded but rather are air-stripped. Some systems treat these air-stripped volatiles in a carbon adsorption filter whereas other systems simply discharge them to the atmosphere.

A fourth system, known as the EIMCO Biolift® system, utilizes a bioreactor that is a tank having a bottom, upstanding walls fixedly mounted thereon and a sealed top or cover, and which is adapted to receive and contain a slurry. The tank is fitted with a mechanical mixing means that operates to effectuate agitation and suspension of the particulates within the slurry housed within the tank. An air supply operates to provide oxygen, which is a necessary component of the biooxidation reaction taking place within the bioreactor. The air supply also is configured to provide suspension of the particulates within the slurry liquid housed within the tank. In addition, an air lift is provided for recirculating particulates which may have settled out of the slurry. The Biolift® system may be operated in continuous mode by using a screening device and exit conduit located near the top inside the tank.

Considerable literature is available describing slurry reactors for municipal and farm sewage digestion, but the total solids for these applications are usually below 10 wt %. The density of sewage sludges is much closer to the density of water than is the density of soil, and therefore the mixing method and design of these sewage sludge stirred reactors can be significantly different than that of soil-slurry reactors. Many sewage digester designs are unstirred, and the predominant mixing mechanism is the $CO_2$ and $CH_4$ gas generated in the reactor. The mixing occurs as these gas bubbles rise through the slurry. Propeller type mixers are sometimes added for more thorough mixing and to try to maintain the solids in suspension. The current design of most soil-slurry reactors is to finely pulverize the material and try to keep it in suspension with significant power input to shaft stirrers, aerators, recirculation pumps or a combination of these methods. The alternative approach is to not mix at all or to mix only occasionally. With the extended residence time required for most biodegradation, there is probably no need for a high shear or complete suspension agitation, especially for an anaerobic design.

In aerobic soil-slurry reactors it is difficult to maintain high oxygen concentrations due to the tendency for gas bubbles to coalesce. Also, since the reactors are usually low in profile, there is a very short liquid-gas contact time and a small surface area to volume ratio of the bubbles. Mechanical agitation is usually required to disperse gas bubbles and give smaller gas bubbles, but as the solids concentration increases the agitation effect decreases.

Common to all hazardous waste treatment systems utilizing microorganism activity is the requirement of providing an adequate supply of nutrients to the microorganisms. This provision allows biomass growth and facilitates the occurrence of biochemical reactions. Various approaches have been used to optimize bioactivity level in reactor vessels. In those systems wherein a multiplicity of connected reactor vessels have been suggested, e.g. cascade systems, a common problem is the retention and maintenance of biomass in a given reactor as effluent from the reactor is directed to the next reactor.

The clean-up of hazardous waste sites requires innovative approaches that are cost effective. Biological systems can play an important role in soil bioremediation, as they have in the field of wastewater treatment. In order to be cost effective in contaminated soil treatment, however, bioreactor vessels and processes are needed that can handle high solids concentrations and large throughput volumes with a minimum of input and/or operating energy.

SUMMARY OF THE INVENTION

The instant invention is a slurry mixer/contactor for a slurry reactor system. The mixer/contactor is particularly well-suited for the biological remediation of contaminated sludges or soils. The reactor system having the slurry mixer/contactor of this invention may operate with microorganisms living in the reactor aerobically or anaerobically. Also, the reactor system may operate with microorganisms in the reactor using oxidative or reductive pathways to biodegrade contaminants. To further increase activity in the bioreactor, additional ingredients, including solids, liquids or gases, may be added to the slurry or suspension in the reactor.

The reactor having the slurry mixer/contactor in one embodiment is an upright generally cylindrical vessel with a flat bottom and a covered top. In the inside of the vessel, along the cylinder centerline, is a vertical conduit extending from near the top to near the bottom. At the bottom of the vertical conduit is the inlet to at least one generally horizontal, hollow, stirrer blade in fluid connection with the vertical conduit. The stirrer blade has outlet openings in it so fluid may pass therethrough. The stirrer blade may rotate around the vertical conduit if the conduit is fixed, or the conduit, with the stirrer blade fixed to it, may rotate around in the vessel. In any event, the rotation of the stirrer blade is caused or made easier by the hydraulic forces of fluid flowing out from the stirrer blade. This rotation may be caused or made easier by a fluidization effect, by a jet propulsion effect, or both. This way, rotation of the stirrer blade may be created or eased near the bottom of the vessel, enhancing mixing of the microorganisms with the sludge or soil in the slurry or suspension in the vessel, without unnecessarily damaging the microorganisms and without having to fluidize the complete vessel contents. Also, this way liquid and/or slurry from near the top of the reactor may be re-distributed into the sediment near the bottom of the reactor for fresh re-contact and further desorption and reaction of contaminants from the sediment to permit further biodegradation.

In a preferred embodiment, the bioreactor vessel has a water recycle outlet port and a gas recycle outlet port. At the water outlet port, which is below the fill line for the reactor, is a water outlet conduit leading to the inlet of a water pump. The pump delivers recycled water back to the bioreactor vessel through a water inlet conduit connected to the vessel at a water recycle inlet port. Preferably, the water inlet port is connected to the vertical conduit in the center of the vessel, and the flow of recycled water provides the hydraulic forces for fluidizing the sediment in the immediate vicinity of the blade and/or the jet propulsion that results in rotation of the stirrer blade.

At the gas outlet port of the bioreactor vessel is a gas outlet conduit leading to the inlet of a gas pump or compressor. The compressor may deliver recycled gas back or fresh gas to the bioreactor vessel through a gas inlet conduit connected to the vessel at a gas recycle inlet port, or connected to the water inlet conduit. This way, water and gas from the bioreactor vessel may be recycled and provided to the vertical conduit to create rotation of the stirrer blade, and better mixing and contacting of the slurry or suspension and the microorganisms in the bioreactor vessel.

Preferably, the slurry mixer/contactor is one, generally horizontal, hollow blade in fluid connection with the vertical conduit. The blade has outlet openings in its leading edge so that fluid passing through the vertical conduit and into the blade may pass out of the blade through the openings. This way, a fluidization zone is created in the sediment, or settled bed of slurry particles, in the region of the openings at the leading edge of the blade. By "leading edge" of the blade is meant the front edge or side of the blade relative to the direction of rotation of the blade. By "trailing edge" is meant the back edge or side of the blade relative to rotation. More than one blade may be used, and blades at various depths in the reactor may also be used. When a plurality of blades is used, they may rotate independently of, or together as a unit with, the other blade(s).

The fluidization zone created by the flow of fluid from the outlet openings in the blade has less density than the rest of the sediment bed throughout the reactor. Therefore, any generally horizontal force on the blade will tend to cause it to rotate into the fluidization zone. This horizontal force on the blade may be created by a propulsion jet at the trailing edge of the blade. Or, this horizontal force may be created by the horizontal component of the weight vector from settling sediment on the rear, downwardly sloping portion of the blade as the sediment descends from a fluidized state to a settled state at the trailing edge of the blade. Or, this horizontal force may be created by the input from an external power source, like an electric motor, for example, connected to and rotating the vessel's vertical conduit. Therefore, the blade rotates, or its rotation in the reactor vessel is made easier, due to the hydraulic forces of fluid flowing out from the stirrer blade.

DETAILED DESCRIPTION OF THE PREFERRED EMBODIMENTS

Figure 1:
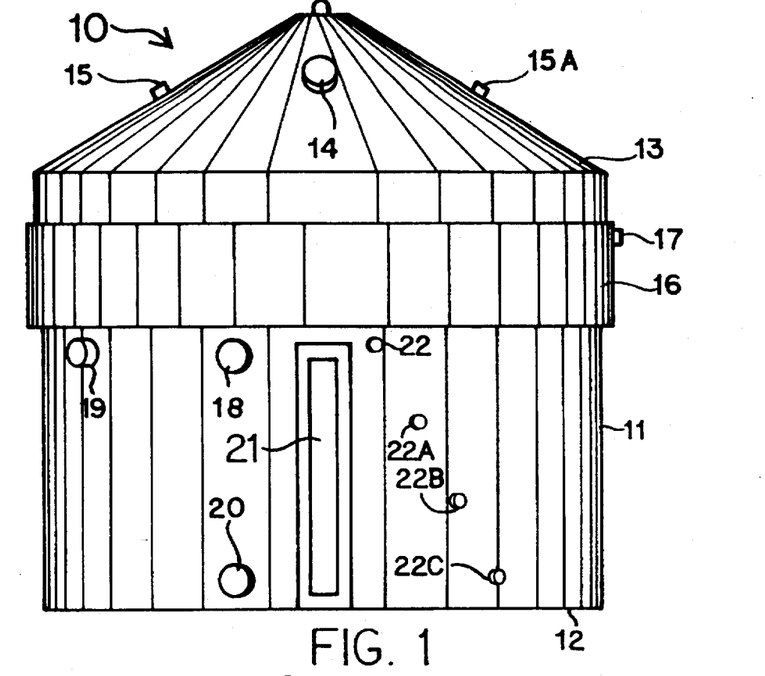
FIG. 1 is a partial side view of one embodiment of the reactor of this invention.

Referring to the Figures, there are shown several, but not the only, embodiments of the slurry reactor 10 having the slurry mixer/contactor of this invention. Referring to FIG. 1, reactor 10 is an upright, generally cylindrical vessel 11 with a flat bottom 12 and a conical top 13. In conical top 13 is optional fill port 14 and gas recycle outlet ports 15 and 15(A). Conical top 13 fits within annular water seal 16, which has water seal overflow port 17. In the side wall of cylindrical vessel 11 are water recycle outlet port 18, water recycle inlet port 19, drain port 20, viewing window 21, and sample ports 22, 22A, 22B, and 22C.

Figure 2:
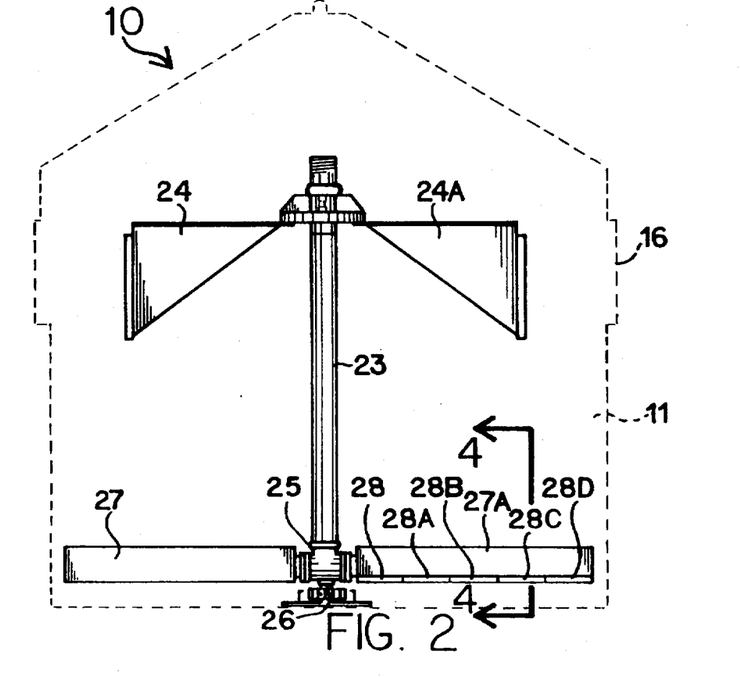
FIG. 2 is a schematic, cross-sectional view of the reactor depicted in FIG. 1, showing some of the reactor's internal structure.

Referring to FIG. 2, reactor 10 has water seal 16 and a vertical conduit 23 supported along the centerline of vessel 11 by bracing 24 and 24A. Vertical conduit 23 terminates near the bottom 12 of vessel 11 at "T" fluid connection 25. "T" connection 25 is rotatably supported on bottom 12 by spindle bearing 26. At the horizontal termini of "T" connection 25 are hollow stirrer blades 27 and 27A. The blades 27 and 27A are in fluid connection with vertical conduit 23, and have in them openings 28, 28A, 28B, 28C, and 28D.

Figure 3:
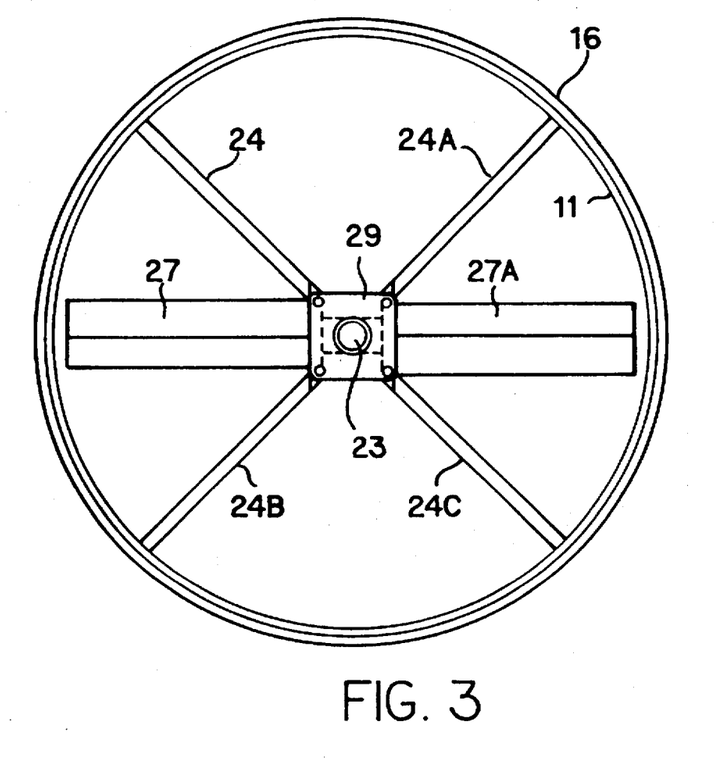
FIG. 3 is a schematic, top cross-sectional view of the reactor depicted in FIGS. 1 and 2.

Referring to FIG. 3, reactor 10 has cylindrical vessel 11 with water seal 16, and bracing 24, 24A, 24B, and 24C for supporting vertical conduit 23. At the bottom end of vertical conduit 23 are horizontal stirrer blades 27 and 27A. In this pictured embodiment, vertical conduit 23 rotates, and it is rotatably supported near its top in the bracing by hub bearing 29.

Figure 4:
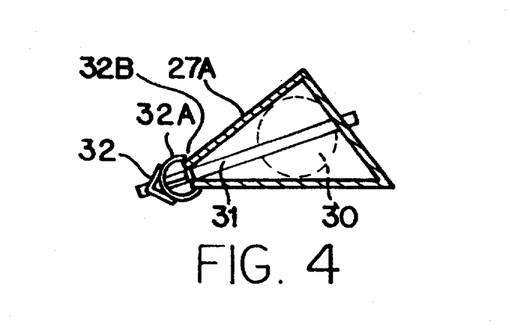
FIG. 4 is a cross-sectional side view of the mixer/contactor blade of the invention, from the line 4—4 in FIG. 2.

Referring to FIG. 4, stirrer blade 27A has a generally triangular cross-sectional shape. The circular "T" connection 25 inlet to the blade 27A is indicated at 30. At several locations along the length of the blade 27A, bolts 31 with leading edge retainers 32 and 32A are provided to stiffen and stabilize blade 27A. A fluid flow path or gap 32B is provided at several locations along the leading length of the blade 27A between it and edge retainer 32A. This way, fluid can exit the blade 27A at gaps 32B and fluidize the sediment bed, and propel the blade around in the reactor.

Figure 5:
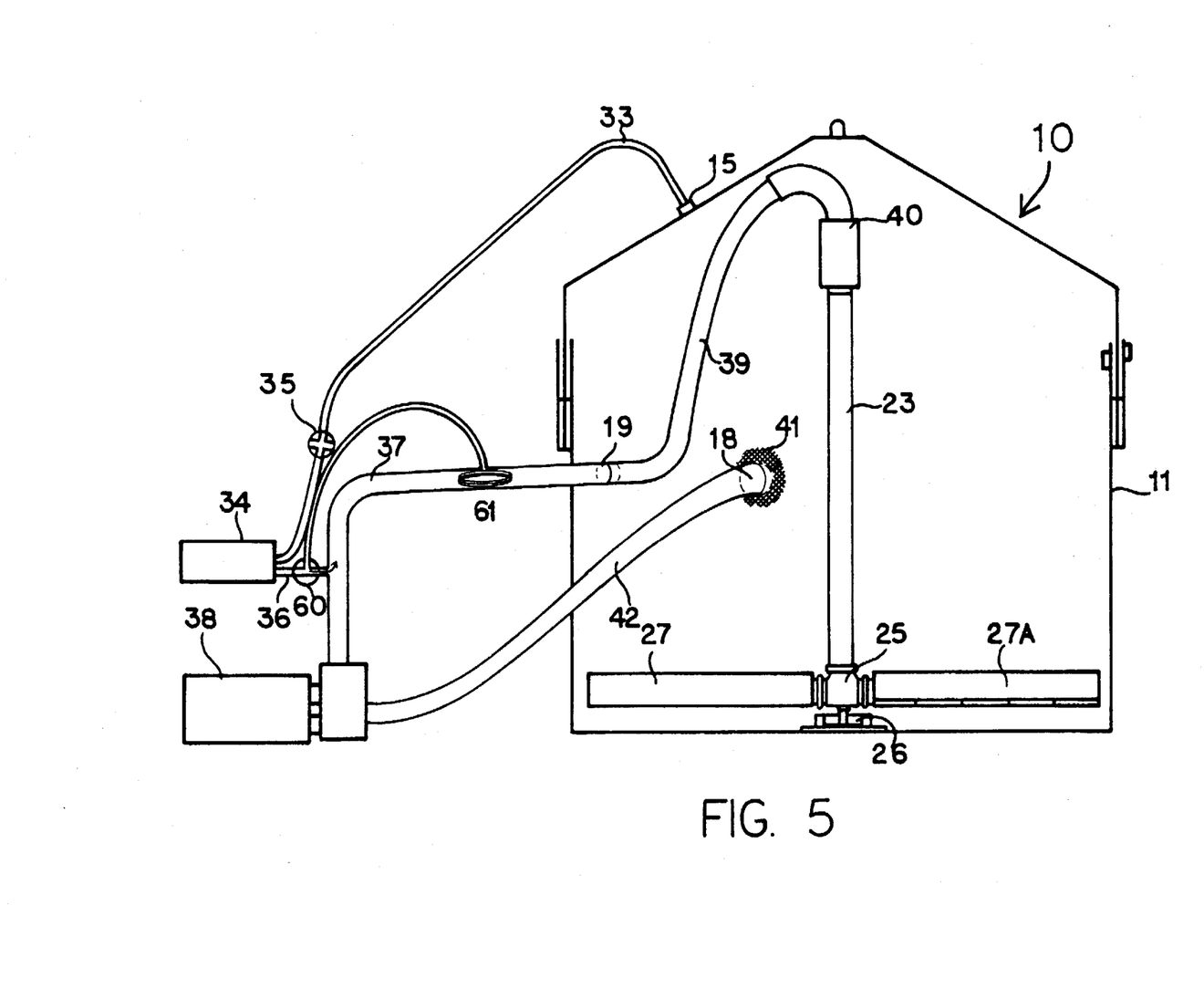
FIG. 5 is a schematic, cross-sectional view of the reactor depicted in FIGS. 1–4, showing the reactor's additional external equipment.

Referring to FIG. 5, reactor 10 has gas recycle outlet port 15 and gas outlet conduit 33 leading to air pump or compressor 34. In outlet conduit 33 is optional 4-way gas valve 35. Air pump 34 discharges compressed recycle gas into gas inlet conduit 36, which is connected and discharges into water recycle inlet conduit 37. Recycle inlet conduit 37 is connected on its first end to water pump 38, and on its second end to water recycle inlet port 19. Inside vessel 11, interior conduit 39 is connected on its first end to inlet port 19, and on its second end to the first end rotating swivel connection 40. Swivel connection 40 is supported by hub 29 in FIG. 3, and connected on its second end to vertical conduit 23. Swivel connection 40 permits interior conduit 39 to be fixably connected to inlet port 19 and swivel connection 40, and, at the same time, permits vertical conduit 23 to be rotatably connected to swivel connection 40. This way, vertical conduit 23, "T" connection 25 and stirrer blades 27 and 27A may rotate inside vessel 11.

During operation, slurry or suspension inside vessel 11 is maintained above the level of water recycle outlet port 18. Outlet port 18 is equipped on the inside of vessel 11 with an outlet screen 41. Screen 41 prevents the solid particles in the slurry or suspension greater than the size of the screen openings from exiting the vessel 11. Water recycle, however, is permitted to exit outlet port 18, and travels via water outlet conduit 42 to the inlet of water pump 38. The discharge of water pump 38 travels via inlet conduit 37, inlet port 19, interior conduit 39, swivel connection 40, vertical conduit 23, "T" connection 25, "T" connection inlet 30, and stirrer blades 27 or 27A back into the interior of vessel 11 near its bottom. This way, the hydraulic forces of the water recycle rotates, or makes easier the rotation or, stirrer blades 27 and 27A, enhancing mixing of the microorganisms with the sludge or settled sediment near the bottom of vessel 11 without unnecessarily damaging the microorganisms. This way, the slurry reactor may be operated with soil slurries at greater than 50 wt % total solids.

Preferably, the bioreactor has four basic modes of operation. In these four modes, the water and air pumps are controlled by a repeat cycle timer that allows either or both pumps to be operated intermittently or continuously.

First Mode.

In the first mode of operation, water is recirculated through the blade which fluidizes the slurry near the blade and propels the stirrer through the slurry, bringing fresh liquid in contact with the soil for rapid mixing. The water exiting the nozzle propels the stirrer and also brings solids up into suspension from the bottom and rapidly mixes them. If the circulation is for a short time, the solids are mixed but not so much that they are fully suspended and sucked into the recycle outlet.

Second Mode.

In the second mode of operation, the air pump can be added to the operation, allowing very efficient aeration for aerobic reactions, and increasing vertical mixing with the rising bubbles. Since the water and air are both under pressure, the amount of oxygen dissolved in the water can be increased considerably above saturation at atmospheric pressure. For high biological oxygen demand (BOD) systems, this will allow significantly higher oxygen mass transfer rates than for a normally bubbled and stirred reactor. If foaming is a problem with a specific slurry or suspension, the addition of air can be intermittent, with the foam subsiding when air is not being added.

One way to add air to the operation is to provide a bubbleless oxygenation tube at the discharge of the air pump or compressor 34. For example, with three-way valve 60 in gas inlet conduit 36 and with bubbleless oxygenator 61 in recycle inlet conduit 37, air under pressure is routed through oxygenator 61 into reactor 11. This way, foaming in reactor 11 may be minimized. Bubbleless oxygenator tubes are available from, for example, Membran Corp., Minneapolis, Minn., U.S.A.

Third Mode.

In the third mode of operation, the air pump will pump headspace gases into the water recycle flow, thereby increasing the mixing rates and allowing the more complete degradation of volatile compounds in the slurry. This will also increase vertical mixing in anaerobic operations and reintroduce volatiles into the slurry for further degradation.

Fourth Mode.

The fourth mode of operation is a combination of the above modes; the modes can be operated on an intermittent basis to reduce operational costs or to maintain microaerophilic conditions. Also, by switching between the second and third modes with the 4-way valve 35, there will be no excess aeration or volatiles lost. This system can be easily interfaced with a computer for active control of the operating mode.

Figure 6:
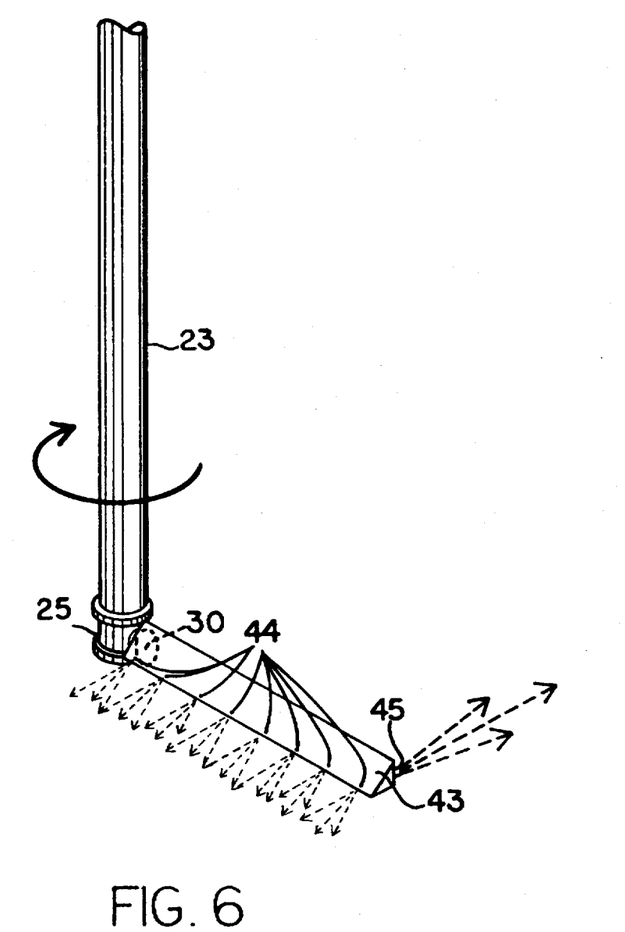
FIG. 6 is a schematic, partial detail isometric view of one embodiment of the slurry mixer/contactor of the invention, showing the fluid flow lines out from it during operation.

Referring to FIG. 6, triangular stirrer blade 43 has fluidization openings 44 in its front, or leading, side, and jet propulsion opening 45 in its back, or trailing, side. When fluid is directed into blade 43 from vertical conduit 23, "T" connector 25 and "T" connector inlet 30, the fluid flows out from fluidization openings 44 and jet propulsion opening 45.

Figure 7:
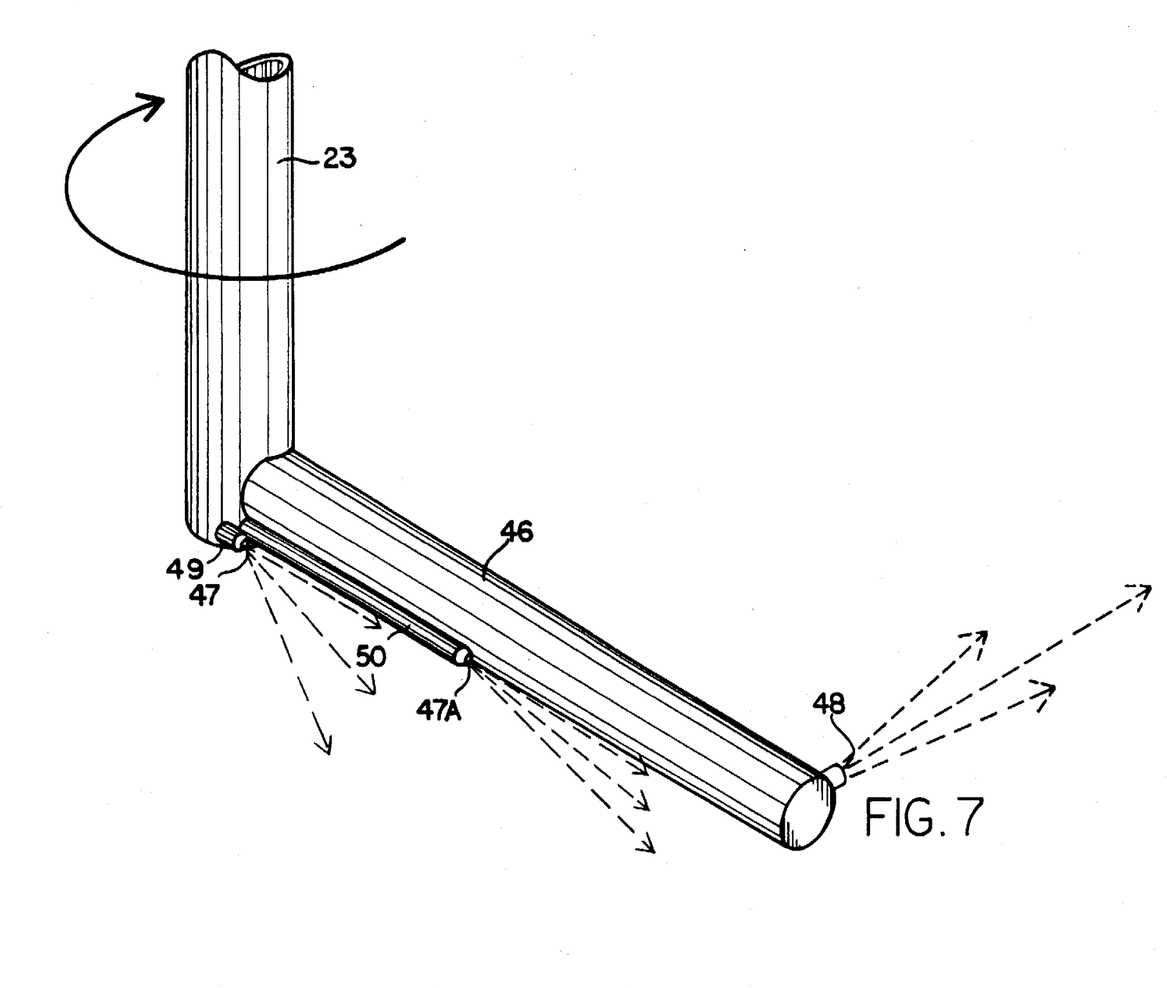
FIG. 7 is a view as in FIG. 6, but of another embodiment of the slurry mixer-contactor.

Referring to FIG. 7, round stirrer blade 46 has fluidization openings 47 and 47A which are the outlets of relatively short conduits welded parallel to the leading edge of blade 46. The conduit 49 is very short and its opening 47 is near vertical conduit 23. The conduit 50 is longer and its opening 47A is near the middle of stirrer blade 46. Both openings 47 and 47A are pointed parallel to the leading edge of blade 46. This way, the fluidization zone created by fluid flowing out of openings 47 and 47A is at or near the leading edge of blade 46. Also, round stirrer blade 46 has jet propulsion opening 48 in its back, or trailing, side.

Figure 8:
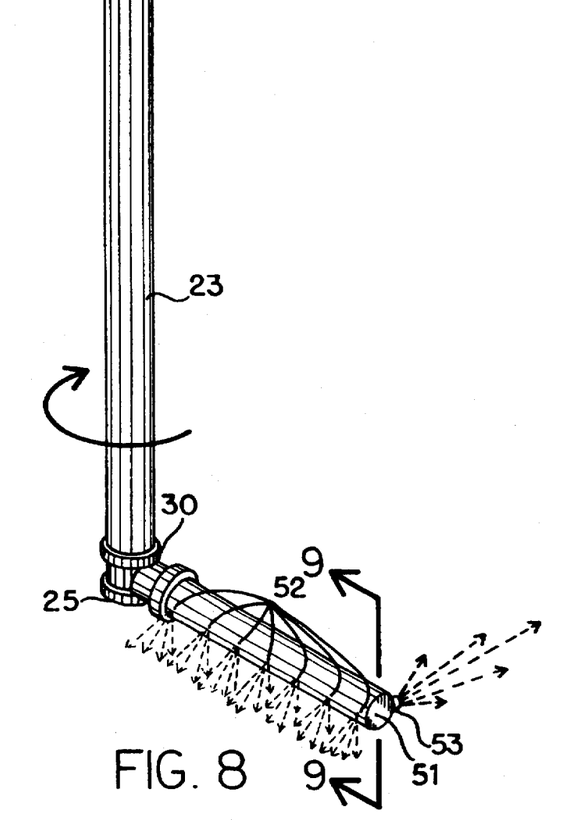
FIG. 8 is a view as in FIGS. 6 and 7, but of yet another embodiment of the slurry mixer-contactor.

Referring to FIG. 8, round stirrer blade 51 has fluidization openings 52 in its front side, and jet propulsion opening 53 in its back side. When fluid is directed into blade 51 from vertical conduit 23, "T" connector 25 and "T" connector inlet 30, the fluid flows out from fluidization openings 52 and jet propulsion opening 53.

Figure 9:
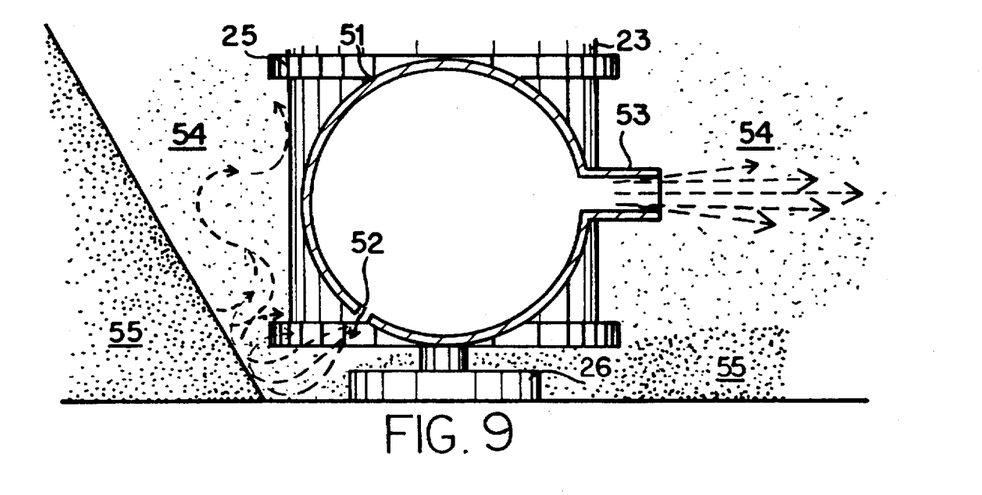
FIG. 9 is a partial, cross-sectional side view from line 9—9 of the mixer/contactor depicted in FIG. 8, showing the fluidization effect and the propulsion effect in the settled bed around it.

Referring to FIG. 9, the outflow of fluid from fluidization openings 52 in stirrer blade 51 creates a zone 54 of fluidized sediment in the region in front of blade 51 near the openings 52. Zone 54 has relatively less density than non-fluidized zone 55 that exists behind blade 51 and elsewhere in the sediment throughout the reactor. Therefore, the tendency is for blade 51 to rotate in the direction of fluidized zone 54 whenever any rotational force is exerted on blade 51, that is, in the direction of the arrow in FIGS. 6-8. This way, blade 51 rotates around the bottom of reactor 10, fluidizing a relatively small segment of the sediment bed before it as it rotates. Also this way, the solid particles that make up the sediment bed are periodically mixed and recontacted with fresh feed or recycle flowing out from openings 52, enhancing desorption of contaminants from them, and biodegradation.

Figure 10:
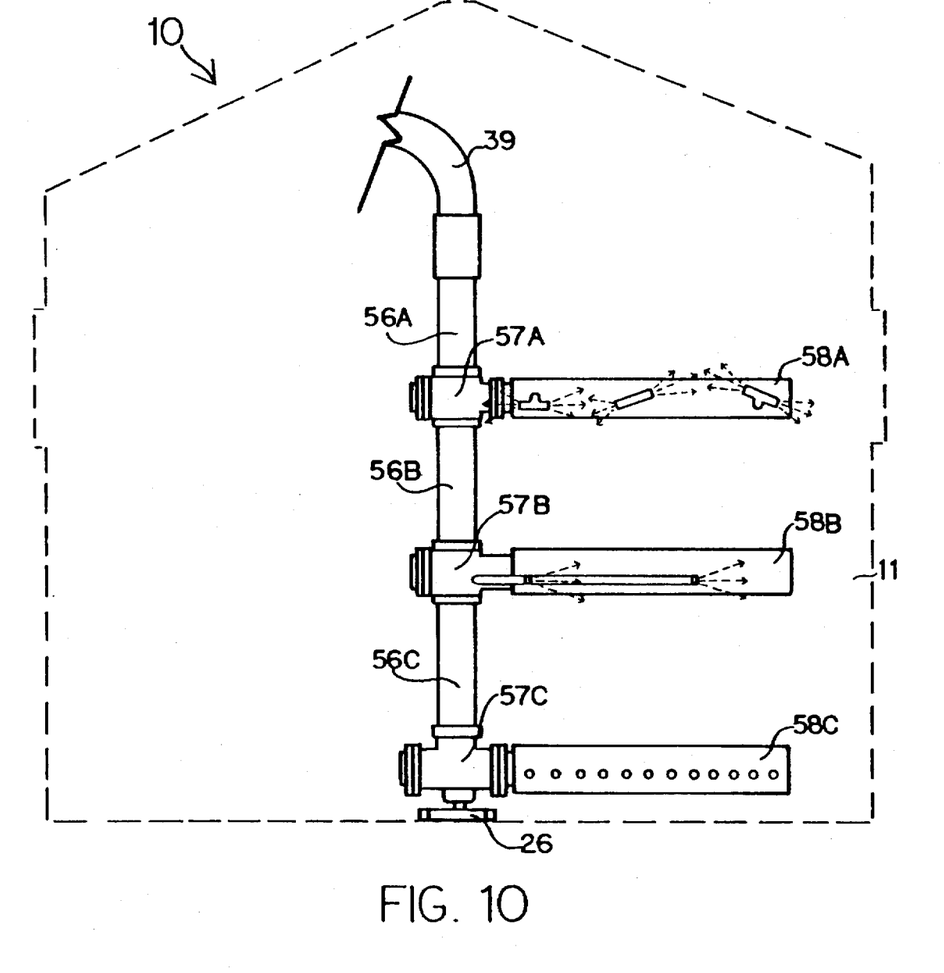
FIG. 10 is a schematic, partial side view of an embodiment of the invention with a plurality of mixer/contactor blades at different depths in the reactor.

Referring to FIG. 10, reactor 10 has several vertical conduits 56A, 56B and 56C, and several rotary unions 57A, 57B and 57C connecting the vertical conduits. Each rotary union has an extending hollow stirrer blade, 58A, 58B and 58C, respectively. Interior conduit 39 is connected to the top of rotary union 57A. The bottom of rotary union 57C is rotatably supported by spindle bearing 26. The blades 58A, 58B and 58C are in fluid connection with the respective rotary unions 57A, 57B and 57C, which in turn are in fluid connection with the respective vertical conduits 56A, 56B and 56C. Depending on the type of rotary union selected, blades 58A, 58B, and 58C may rotate independently of one another, in combination or all together as a unit.

The stirrer or mixer/contactor blade of this invention, then, may be practiced in several embodiments. The size and shape of the blade may be varied, as long as outlet openings may be placed near its leading edge. Preferably, the blade has a shape which encourages sediment settling on it to be directed towards the trailing edge of the blade as the sediment continues to descend. With such a shape, the horizontal component of the weight vector from the settling sediment pushes the blade forward into the fluidization zone at the front of the blade. For example, the blade may be shaped to have a side profile similar in general to an airplane wing. When the blade is shaped appropriately, adequate forward horizontal force is supplied by the settling sediment, making optional the propulsion jet openings at the trailing edge of the blade.

So, the selection or design of a particular blade for use in the invention depends upon many factors, including: the type of liquid and the size and density distributions of the solid particles; the rate of the biodegradation reactions; etc. Therefore, a preferred blade design depends upon many factors like these.

It is also apparent that adding a motorized device to assure rotation of the blade that has material fluidized in the immediate vicinity of the blade would fall within the scope of this invention. One main aspect of this invention is to provide energy to fluidize material in the immediate vicinity of the blade and then move this fluidized zone around the complete reactor. Whether or not the rotational force comes solely from the hydraulic forces or also from a mechanical torque provider is also within the scope of this invention.

Although this invention has been described above with reference to particular means, materials and embodiments, it is to be understood that the invention is not limited to these disclosed particulars, but extends instead to all equivalents within the scope of the following claims.

I claim:

1. A stirrer blade for a bioslurry reactor and for connection to a fluid source, said stirrer blade comprising:

a first end and a second end;

a leading side and a dissimilar trailing side;

a hollow space and a fluid inlet to the hollow space near the blade first end for connection with a fluid source;

the stirrer blade leading side having a fluid outlet opening from the hollow space; and said stirrer blade being without mechanical drive means.

2. A stirrer blade as set forth in claim 1, wherein the stirrer blade leading side comprises a conduit extending parallel to the leading side and being shorter than the length of the blade, the conduit having a fluid inlet near the blade first end for connection with the fluid source, a hollow interior, and having an open end that is said stirrer blade fluid outlet opening.

3. A stirrer blade as set forth in claim 1, wherein the stirrer blade comprises an elongated member having a leading side and a dissimilar trailing side, an end with an opening in fluid connection with the fluid source, a hollow interior, and a plurality of openings along said leading side for fluid outlet from said hollow interior.

4. A stirrer blade as set forth in claim 1, wherein the stirrer blade comprises an elongated cylindrical member, having a leading side and a dissimilar trailing side, an end with an opening in fluid connection with the fluid source, and a hollow interior, and wherein said leading side has a plurality of openings for fluid outlet from said hollow interior, and said trailing side does not have a plurality of openings for fluid outlet from said hollow interior.

5. A stirrer blade for a bioslurry reactor, the stirrer blade for connection to a fluid source and said blade comprising:

a first end and a second end;

a leading side and a dissimilar trailing side;

the stirrer blade leading side comprising a conduit extending along the leading side, said conduit having a fluid inlet near said stirrer blade first end for connection with a fluid source, a hollow interior, and having an open end for fluid flow out from the hollow interior.

6. A stirrer blade as set forth in claim 5, wherein said conduit is parallel to the leading side.

7. A stirrer blade for a bioslurry reactor, the stirrer blade for connection to a fluid source and said blade comprising:

an elongated member having a first end with an opening in fluid connection with a fluid source, a hollow interior, a second end, a leading side and a dissimilar trailing side; and wherein said leading side has a plurality of openings for fluid outlet from said hollow interior directed at or near said leading side.

8. A stirrer blade as set forth in claim 7, wherein said elongated member is cylindrical, and said trailing side does not have a plurality of openings for fluid outlet from said interior.

9. A slurry reactor comprising:

a vessel for containing a liquid slurry or suspension of solid particles or a settled bed of solid particles in a fluid;

a conduit extending into the interior of said vessel, said conduit being constructed to receive fluid directed to the interior of said vessel;

a stirrer blade within said vessel, said blade being in fluid and rotatable connection with said conduit, said stirrer blade having a first end, a second end, a hollow space and a fluid inlet to the hollow space of the blade near the blade first end for fluid connection with said conduit, and said stirrer blade having a leading side and a dissimilar trailing side, said leading side having a fluid outlet opening, so that, when a fluid is directed to the interior of said vessel through said conduit, said fluid flows into said stirrer blade and out from it through said fluid outlet opening and said stirrer blade fluidizes the solid particles near the leading side of the blade as a result of the flow of said fluid through said opening, moves more easily through said liquid slurry or suspension or settled bed, and provides agitation of said solid particles within said vessel; and said stirrer blade being able to move without requiring mechanical drive means.

10. A reactor as set forth in claim 9, wherein there is a single stirrer blade.

11. A reactor as set forth in claim 9, wherein there is a plurality of stirrer blades.

12. A reactor as set forth in claim 11, wherein the blades are constructed to rotate independently of one another.

13. A reactor as set forth in claim 11, wherein the blades are constructed to rotate together as a unit.

14. A reactor as set forth in claim 11, wherein the blades are at different depths in the reactor.

15. A slurry reactor comprising:

a vessel for containing a liquid slurry or suspension of solid particles or a settled bed of solid particles in a fluid;

a supply conduit extending into the interior of said vessel, said supply conduit being constructed to receive fluid directed to the interior of said vessel; and a stirrer blade within said vessel, said blade being in fluid and rotatable connection with said supply conduit, said stirrer blade having a first end, a second end, a hollow space and a fluid inlet to the hollow space of the blade near the blade first end for fluid connection with said supply conduit, and said stirrer blade having a leading side and a dissimilar trailing side, said leading side having a fluid outlet opening, so that, when a fluid is directed to the interior of said vessel through said supply conduit, said fluid flows into said stirrer blade and out from it through said fluid outlet opening and said stirrer blade fluidizes near the leading side of the blade as a result of the flow of said fluid through said opening, moves more easily through said liquid slurry or suspension or settled bed, and provides agitation of said solid particles within said vessel; and wherein said stirrer blade leading side comprises a stirrer blade conduit extending along the stirrer blade leading side, the stirrer blade conduit having a fluid inlet connected to said supply conduit, a hollow interior, and having an open end that is said fluid outlet opening.

16. A slurry reactor as set forth in claim 15, wherein said stirrer blade conduit is parallel to the stirrer blade leading side.

17. A slurry reactor comprising:

a vessel for containing a liquid slurry or suspension of solid particles or a settled bed of solid particles in a fluid;

a supply conduit extending into the interior of said vessel, said supply conduit being constructed to receive fluid directed to the interior of said vessel; and a stirrer blade within said vessel, said blade being in fluid and rotatable connection with said supply conduit, said stirrer blade having a first end, a second end, a hollow space and a fluid inlet to the hollow space of the blade near the blade first end for fluid connection with said supply conduit, and said stirrer blade having a leading side and a dissimilar trailing side, said leading side having a fluid outlet opening, so that, when a fluid is directed to the interior of said vessel through said supply conduit, said fluid flows into said stirrer blade and out from it through said opening and said stirrer blade fluidizes the solid particles near the leading side of the blade as a result of the flow of said fluid through said opening, moves more easily through said liquid slurry or suspension or settled bed, and provides agitation of said solid particles within said vessel; and wherein said stirrer blade leading side comprises an elongated member having a leading side and a dissimilar trailing side, an end with an opening in fluid connection with the supply conduit, a hollow interior, and a plurality of openings along said leading side for fluid outlet from said hollow interior directed at or near said leading side.

18. A slurry reactor as set forth in claim 17, wherein said stirrer blade elongated member is cylindrical and said trailing side does not have a plurality of openings for fluid outlet from said hollow interior.

19. A method for operating a slurry reactor which comprises:

providing a liquid slurry or suspension of solid particles or a settled bed of slurry particles in a reactor vessel;

directing fluid flow through a supply conduit to the liquid slurry or suspension or settled bed within said reactor vessel;

passing said fluid flow through a stirrer blade within said reactor vessel, said stirrer blade being in fluid and rotatable connection with said supply conduit, said stirrer blade having a first end, a second end, a hollow space and a fluid inlet to the hollow space of the blade near the blade first end for fluid connection with said supply conduit, and said stirrer blade having a leading side and a dissimilar trailing side, said leading side having a fluid outlet opening, so that the stirrer blade fluidizes the solid particles near the leading side of the blade as a result of the flow of said fluid through said opening, moves more easily through said liquid slurry or suspension or settled bed, and provides agitation of said solid particles within said reactor vessel; and not providing any motorized force to said stirrer blade.

20. A method as set forth in claim 19, wherein said fluid flow is directed intermittently to the liquid slurry or suspension or settled bed.

21. A method as set forth in claim 19, wherein air is added to the fluid flow.

22. A method as set forth in claim 19, wherein a gas is added to the fluid flow.

23. A method as set forth in claim 22, wherein said gas is added to the fluid flow through a bubbleless gas dissolution device.

24. A method as set forth in claim 19, wherein gas is collected from the top of the reactor vessel and recycled to the liquid slurry or suspension or settled bed within the reactor.

25. A method as set forth in claim 19, wherein water is collected from the reactor vessel and recycled to the liquid slurry or suspension or settled bed within the reactor.

26. A method as set forth in claim 19, wherein the fluid flow is passed through a plurality of stirrer blades.

27. A method as set forth in claim 26, wherein the stirrer blades move independently of one another.

28. A method as set forth in claim 26, wherein the stirrer blades move together as a unit.

* * * * *